(12) United States Patent
Kahn et al.

(10) Patent No.: US 9,072,596 B1
(45) Date of Patent: Jul. 7, 2015

(54) TRANSJUGULAR INTRAHEPATIC PORTOSYSTEMIC SHUNT DEVICE

(71) Applicants: Sidney Lowell Kahn, Somers, CT (US); Wael Saad, Charlottesville, VA (US); Brent Seybold, Santa Clara, CA (US)

(72) Inventors: Sidney Lowell Kahn, Somers, CT (US); Wael Saad, Charlottesville, VA (US); Brent Seybold, Santa Clara, CA (US)

( * ) Notice: Subject to any disclaimer, the term of this patent is extended or adjusted under 35 U.S.C. 154(b) by 375 days.

(21) Appl. No.: 13/651,682

(22) Filed: Oct. 15, 2012

(51) Int. Cl.
*A61M 5/00* (2006.01)
*A61M 5/32* (2006.01)
*A61F 2/06* (2013.01)
*A61M 27/00* (2006.01)

(52) U.S. Cl.
CPC .............. *A61F 2/06* (2013.01); *A61M 27/002* (2013.01)

(58) Field of Classification Search
USPC ............... 604/8–10, 27, 30, 35–38, 171, 173, 604/176; 623/1.11
See application file for complete search history.

(56) References Cited

U.S. PATENT DOCUMENTS

| 2002/0198588 A1 | 12/2002 | Armstrong et al. |
| 2005/0020963 A1 * | 1/2005 | Gabal .............................. 604/8 |

* cited by examiner

*Primary Examiner* — Philip R Wiest
(74) *Attorney, Agent, or Firm* — Malin, Haley, DiMaggio & Bowen, P.A.

(57) ABSTRACT

An apparatus method for establishing a Transjugular Intrahepatic Portosystemic Shunt between the portal vein from a hepatic vein. The apparatus comprises an elongated hollow outer guide; an outer handle having an inner lumen and a first luer lock, the outer handle attached at a proximal end of the outer guide, the outer guide in flow communication with the inner lumen and the luer lock; an elongated hollow inner needle; and a hub having a second luer lock, the hub attached at a proximal end of the inner needle, the inner needle in flow communication with the second luer lock. The inner needle is slidingly received into the outer guide through the inner lumen. The inner needle is configured to rotate within the outer guide by manipulation of the hub; and a distal tip of the inner needle is deployed out of and beyond a distal tip of the outer guide.

7 Claims, 17 Drawing Sheets

TRANSJUGULAR INTRAHEPATIC PORTOSYSTEMIC SHUNT DEVICE

CROSS REFERENCE TO RELATED APPLICATIONS

This application is a continuation-in-part of U.S. patent application Ser. No. 12/644,452 filed on Dec. 22, 2009 which claims the benefit of U.S. Provisional Application No. 61/140,693 filed Dec. 24, 2008.

BACKGROUND OF THE INVENTION

1. Field of the Invention

The present invention relates to an apparatus and method for quickly locating a liver portal vein to establish a shunt through a human liver between the portal vein and the hepatic vein, and more particularly to a Transjugular Intrahepatic Portosystemic Shunt ("TIPS") device and a method for establishing a TIPS using the device.

2. Description of Related Art

The human liver has many functions essential to life including breaking down fats, glucose metabolism/storage, urea production, amino acid synthesis, toxin filtration, storage of vitamins and minerals, and cholesterol metabolism. On average, the healthy liver receives around 70-75% of its blood supply from the portal vein and 25-30% from the hepatic artery. Blood leaves the liver through the hepatic veins which communicate with the inferior vena cava just below the heart.

Liver cirrhosis is a term that refers to irreparable damage to the liver where the hepatic parenchyma is progressively replaced with scar tissue. With time, this can progress to complete liver failure. There are numerous causes of liver cirrhosis, but common causes include alcohol abuse, hepatitis, non-alcoholic steatohepatitis (NASH), toxin/drug exposure, and various inherited and autoimmune conditions. As the liver becomes cirrhotic, the normal blood flow patterns become altered. Specifically, the pressure within the portal veins increases causing the blood that would normally flow to the liver to "back-up." Over time the portal blood that normally flows towards the liver (hepatopedal) can reverse and flow away from the liver (hepatofugal). As the portal vein pressures rise, the blood finds alternative routes to return to the heart. This typically occurs in the form of variceal vessels that are particularly prone to hemorrhage with potentially fatal consequences.

In addition, the increased portal vein pressures observed with cirrhosis raises capillary hydrostatic pressures within the splanchnic vascular bed of the viscera. As the hydrostatic pressure rises, a transudative fluid collection, known as ascites, can form in the patient's abdomen. Although typically this is initially managed with medical therapy, the amount of fluid can become quite large and refractory to medical therapy.

Originally described by Rosch et al. in 1969, the TIPS procedure creates a shunt between the portal veins and the hepatic veins allowing blood to bypass the cirrhotic hepatic parenchyma that is responsible for the elevated portal vein pressures. In so doing, the TIPS procedure decreases portal pressure and is indicated in the management of variceal bleeding refractory to medical therapy, refractory ascites, and refractory hepatic hydrothorax (fluid surrounding the lungs secondary to liver failure).

There are several commercially available kits for the TIPS procedure. The TIPS procedure is performed under general anesthesia by accessing the patient's right internal jugular vein and advancing a catheter through the superior vena cava, heart, and inferior vena cava to the right hepatic vein. Once catheter access to the right hepatic vein is made, a larger sheath is then placed into the right hepatic vein. Through this sheath a large needle (typically 16 Gauge) is pushed through the wall of the hepatic vein into the parenchyma anteromedially in the expected direction of the right portal vein. After the needle has been advanced, a syringe is attached to the back of the needle and the needle is slowly withdrawn. When blood is aspirated, a small injection of contrast is made into the needle to confirm access into the right portal vein. Wire access through the needle into the right portal vein and main portal vein is then made. Over this wire, a tract is balloon dilated and a covered stent is placed thus forming the shunt.

Despite the use of preprocedural imaging as well as intraprocedural wedge portography, access to the portal vein can often prove difficult requiring numerous passes of the needle before access is obtained. The passage of the needle through the liver is associated with complications including intraperitoneal bleeding (frequency 1-13%), hemobilia (frequency 1-4%), and fistula formation (frequency <1%). Equally important, the difficulty of portal vein access extends procedure time with the increased use of hospital resources/expenses and the added risk to the patient of prolonged anesthesia. Therefore, there is a need for a TIPS device and method that can obtain access to the portal vein more safely and rapidly.

SUMMARY OF THE INVENTION

The present invention relates to a device that is designed to improve the safety and efficacy of catheterization of the portal vein during a TIPS procedure and a method for using the device. This is accomplished by simultaneously advancing multiple smaller needles through the liver parenchyma from the distal end of the TIPS needle of the device. In so doing, the device allows sampling from a significantly larger volume of the liver with each pass thereby facilitating the rapid catheterization of the portal vein from the hepatic vein.

The proposed device is superior to the prior art because it employs a plurality of needles, each smaller than the needle used in a typical TIPS procedure, that are simultaneously advanced into the hepatic parenchyma. The needles will spread apart in area progressively as they are manually advanced into the hepatic parenchyma with the tips forming a square or polygonal pattern accordingly. The use of multiple needles multiplies the likelihood of catheterizing the portal vasculature and reduces the time in which the this is done compared to passage of a single needle as is typically employed in a TIPS procedure.

In addition, the needles used in this device are considerably smaller than the 16 Gauge needle used in a typical TIPS procedure. The present invention uses needles as small as 21 or 23 Gauge. The use of smaller needles is less traumatic to the vascular liver. It therefore will decrease the likelihood of potentially fatal complications, including hemorrhage, hemobilia, fistula creation, and injury to adjacent organs. The larger needle that houses these smaller needles will only be advanced a very short distance into the hepatic parenchyma and therefore is much less invasive.

An additional embodiment of the invention includes an insertion apparatus comprising an outer guide with either a straight (discussed in the next paragraph) or steerable inner needle. The assembled apparatus with the steerable needle allows the needle to be directed in the same direction as the outer guide. The steerable needle can be directed in any direction along a 360 degree arc. The employment of a steerable inner needle enhances the ease of portal vein catheterization by allowing the operator to steer the needle in the expected direction of the portal vein. This confers the same advantages of the multi-needle embodiment, including decreased procedure time and enhanced safety. The reduced procedure time confers advantages of cost-savings, decreased anesthesia risk to the patient, and decreased radiation exposure to both the patient and the operator. A further embodiment of this apparatus includes the substitution of the curved inner needle (which allows steering) for a straight inner needle (non-steerable). This would be used in the event that the operator believes the portal vein lies directly in front of the curved outer guide. In such a situation a straight needle would be optimal for portal vein catheterization as it provides a more direct route.

In some embodiments, this apparatus comprises an elongated hollow outer guide; an outer handle having an inner lumen and a first luer lock, the outer handle attached at a proximal end of the outer guide, the outer guide in flow communication with the inner lumen and the luer lock; an elongated hollow inner needle; and a hub having a second luer lock, the hub attached at a proximal end of the inner needle, the inner needle in flow communication with the second luer lock. The inner needle is slidingly received through the first luer lock and into the outer guide through the inner lumen. The inner needle is configured to rotate within the outer guide by manipulation of the hub; and a distal tip of the inner needle is deployed out of and beyond a distal tip of the outer guide, the distal tip of the inner needle configured to be advanced into the parenchyma of the liver to locate the portal vein. To assist in located the portal vein, the inner needle is capable of aspirating fluid therethrough.

The present invention also comprising a method of locating a liver portal vein necessary for performing a transjugular intrahepatic portosystemic shunt procedure utilizing the outer guide/inner needle device, comprising catheterizing, through the jugular vein, a liver hepatic vein of a patient receiving the transjugular intrahepatic portosystemic shunt. Inserting the device into the jugular vein and through to the liver hepatic vein. Rotating the outer handle of the device until the outer guide is in the expected direction of the liver portal vein. Stabilizing the outer handle and rotating the inner needle by way of the hub in the expected direction of the liver portal vein. Applying pressure to the hub and advancing the distal tip of the inner needle into the parenchyma of the liver, through the wall of the of the hepatic vein in a direction towards the portal vein. Creating an aspirating force inside the inner needle to locate the liver portal vein and establishing a shunt to the portal vein.

Consequently, the devices described herein will result in considerable cost savings and improved safety by shortening the length of time of the procedure. The decrease in procedural time is significant as it lowers the rate of complications related to the administration of general anesthesia. Moreover, the decrease in procedural time offers cost savings benefits to the healthcare system.

In another embodiment, the device employs 6 smaller needles that extend from the distal end of a TIPS needle.

In yet another embodiment, the device employs 8 smaller needles that extend from the distal end of a TIPS needle.

In yet still another embodiment, the device employs only one sheath in which the TIPS needle passes through.

In yet still another embodiment, the device employs an outer guide receiving a steerable curved inner needle and an apparatus for the manipulation of the inner needle to locate the portal vein during a TIPS procedure.

It is an object of the present invention to provide a multi-needled TIPS device that can obtain access to the portal vein from the hepatic vein more safely and rapidly.

It is another object of the present invention to provide a method for using the multi-needled TIPS device to reduce the time necessary to establish a shunt.

In accordance with these and other objects which will become apparent hereinafter, the instant invention will now be described with particular reference to the accompanying drawings.

DETAILED DESCRIPTION OF THE INVENTION

Figure 1:
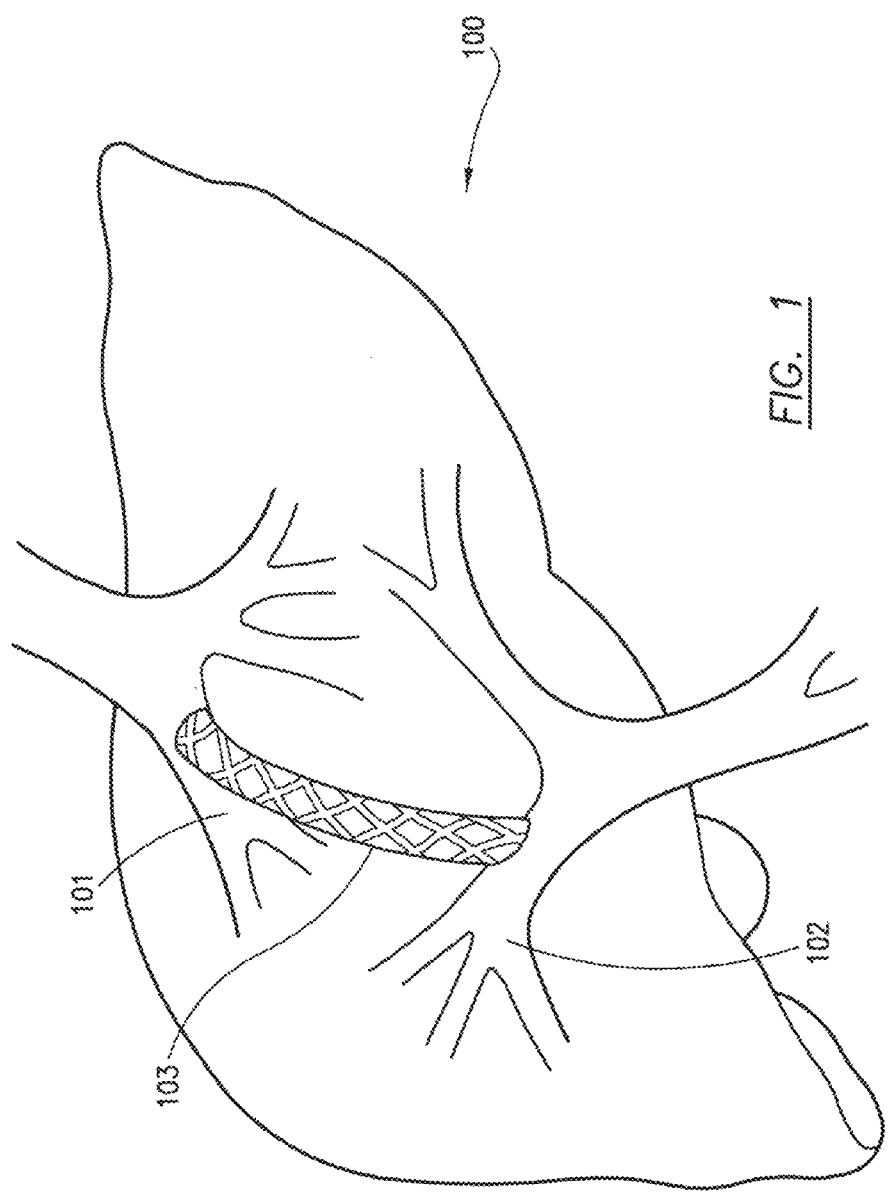
FIG. 1 is a drawing to illustrate a human liver, the hepatic vein, and the portal vein.

A multi-needle TIPS device and a method for using the multi-needle TIPS device, in accordance with the present invention, are described with initial reference to FIG. 1. The device and method described herein is desirable for locating quickly the proper portal vein for establishing a shunt 103 through a human liver 100, connecting the right hepatic vein 101 to the right portal vein 102.

Figure 2:
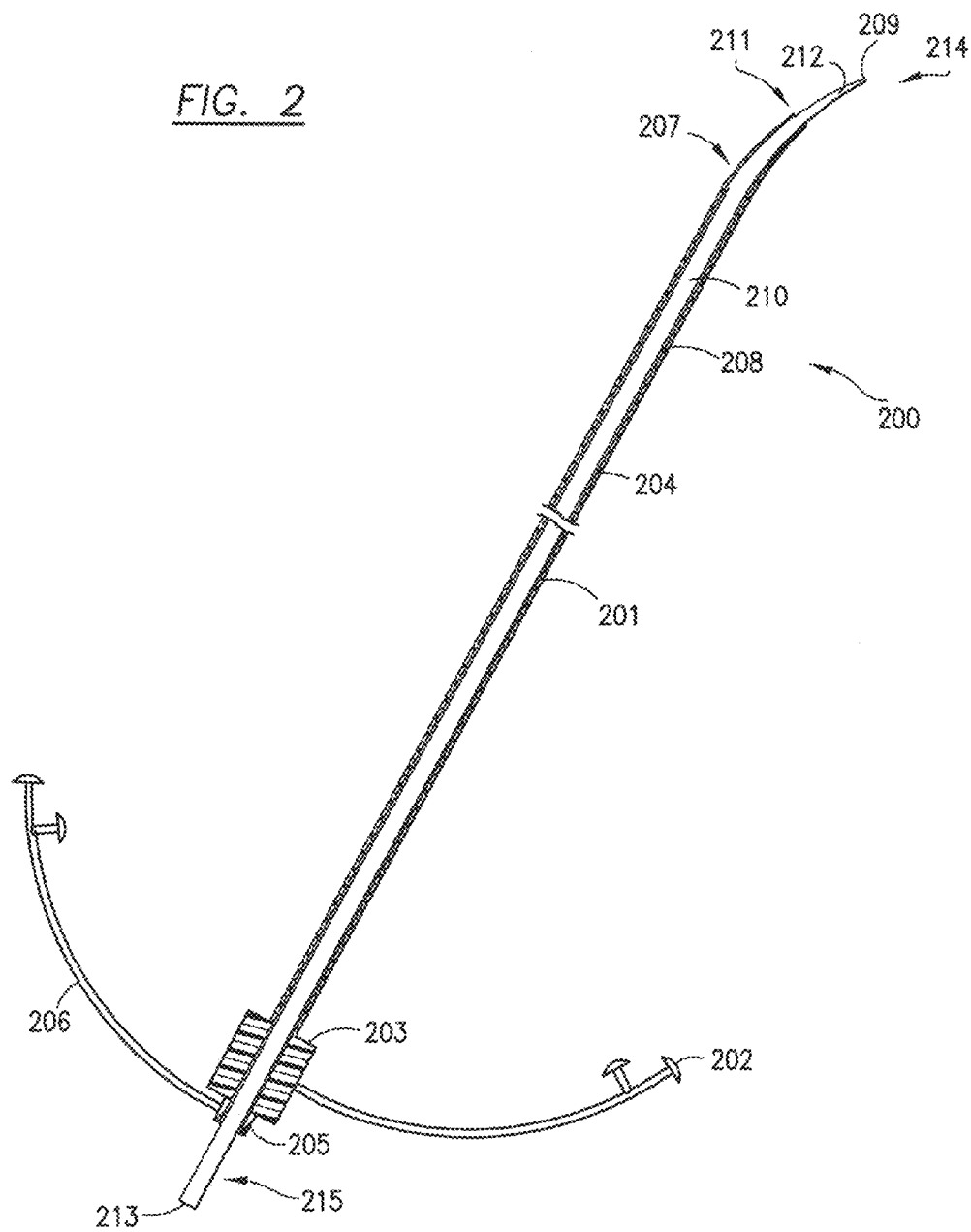
FIG. 2 is a side cross-sectional view in elevation of the present invention in a retracted state.
Figure 3:
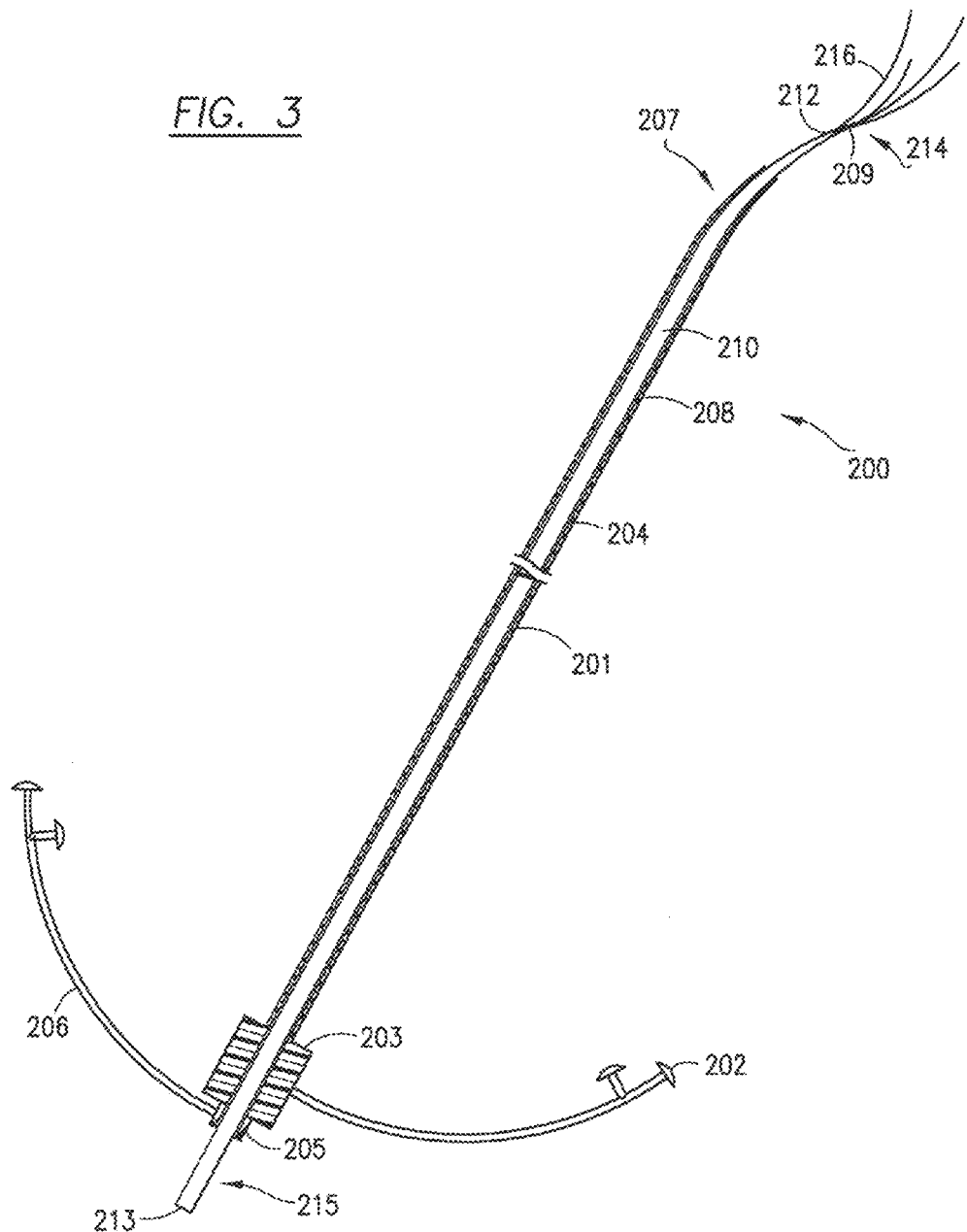
FIG. 3 is a side cross-sectional view in elevation of the present invention in an extended state.
Figure 4:
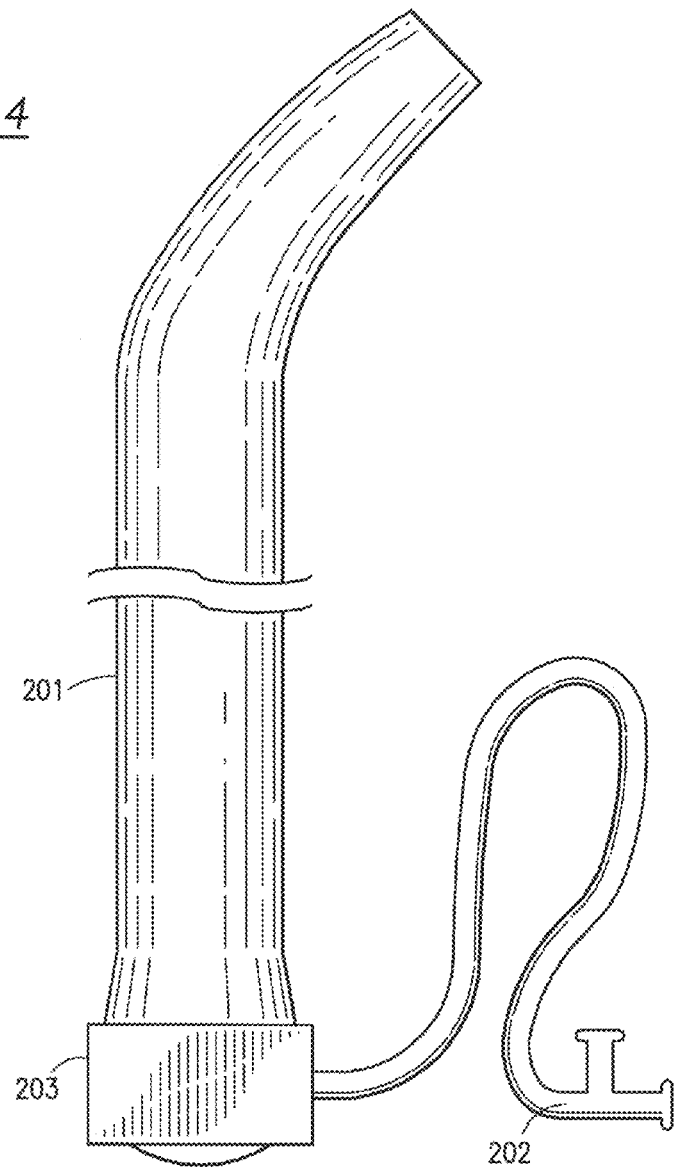
FIG. 4 is a side elevational view partially cut away of an outer sheath built in accordance with the present invention.

Referring now to FIGS. 2, 3, 4, 5, 6, and 7, the device 200 and its primary components are depicted in isolation and in a retracted and extended state. FIG. 2 shows the device 200 in the retracted state, which is a non-engaging, default state. An outer sheath 201 is the primary exterior component of the device 200. The outer sheath comes with an inner dilator to allow introduction over a wire into the right hepatic vein. The outer sheath 201 is a ten (10) French sheath which is made of a semi-rigid material. In FIG. 4, the outer sheath 201 has a shaft that measures between 35 and 40 cm in length and an outer hub 203 with an outer side port 202 at its proximal end that is designed to allow flushing of the outer sheath 201.

Figure 5:
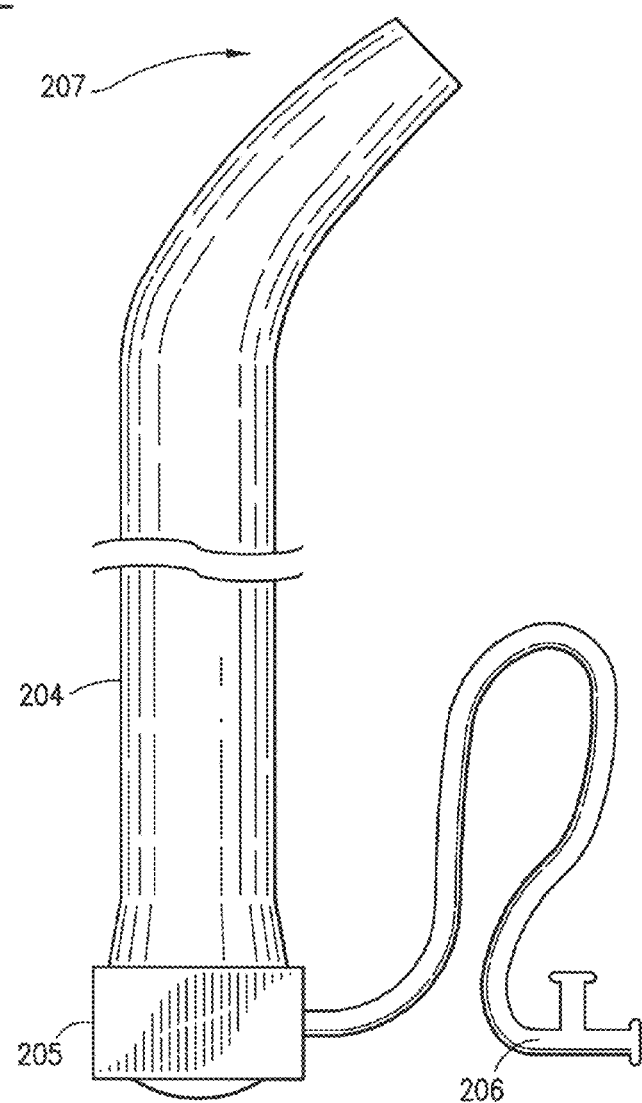
FIG. 5 is a side elevational view partially cut away of an inner sheath built in accordance with the present invention.
Figure 6:
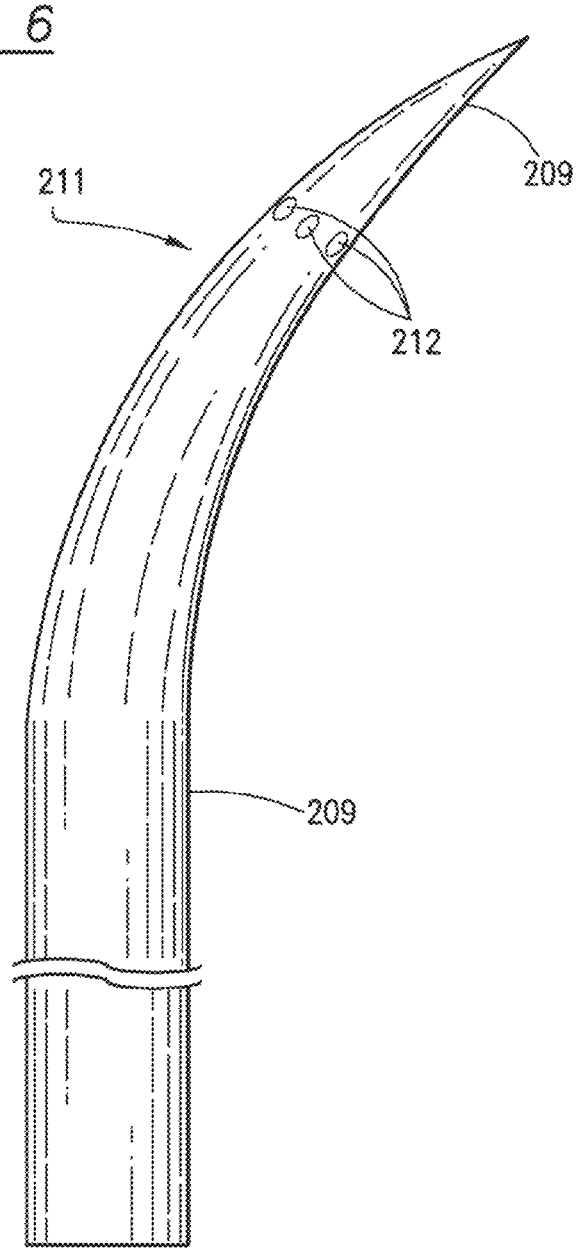
FIG. 6 is a side elevational view of a TIPS needle in a retracted state built in accordance with the present invention.

In FIG. 5, the lumen of the outer sheath 201 accommodates an inner sheath 204. The inner sheath 204 is an eight (8) French sheath which is made of a semi-rigid material. The shaft of the inner sheath measures 45 cm in length has a tapered end 207. The inner sheath 204 also has an inner hub 205 and inner side port 206 at its proximal end to allow for flushing of the inner sheath 204. The shaft of the inner sheath 204 also has a braided metallic wall to allow passage of an 8 French needle without damage to the inner sheath 204.

The lumen of the inner sheath 204 accommodates a TIPS needle 208, which in total measures 50 cm in length, including a curved portion 211 of 7 cm at the TIPS needle's distal end 214. The TIPS needle is an eight (8) French needle made of a semi-rigid material. The curved portion 211 has a 30 degree curve. At distal end of the TIPS needle 208 is a TIPS needle tip 209 (See FIG. 6). Near the distal end of the TIPS needle 208, before the TIPS needle tip 209, there are four needle holes 212 designed to allow smaller needles to pass through. The TIPS needle also has a TIPS needle hub 213 at the proximal end 215 of the TIPS needle.

Figure 7:
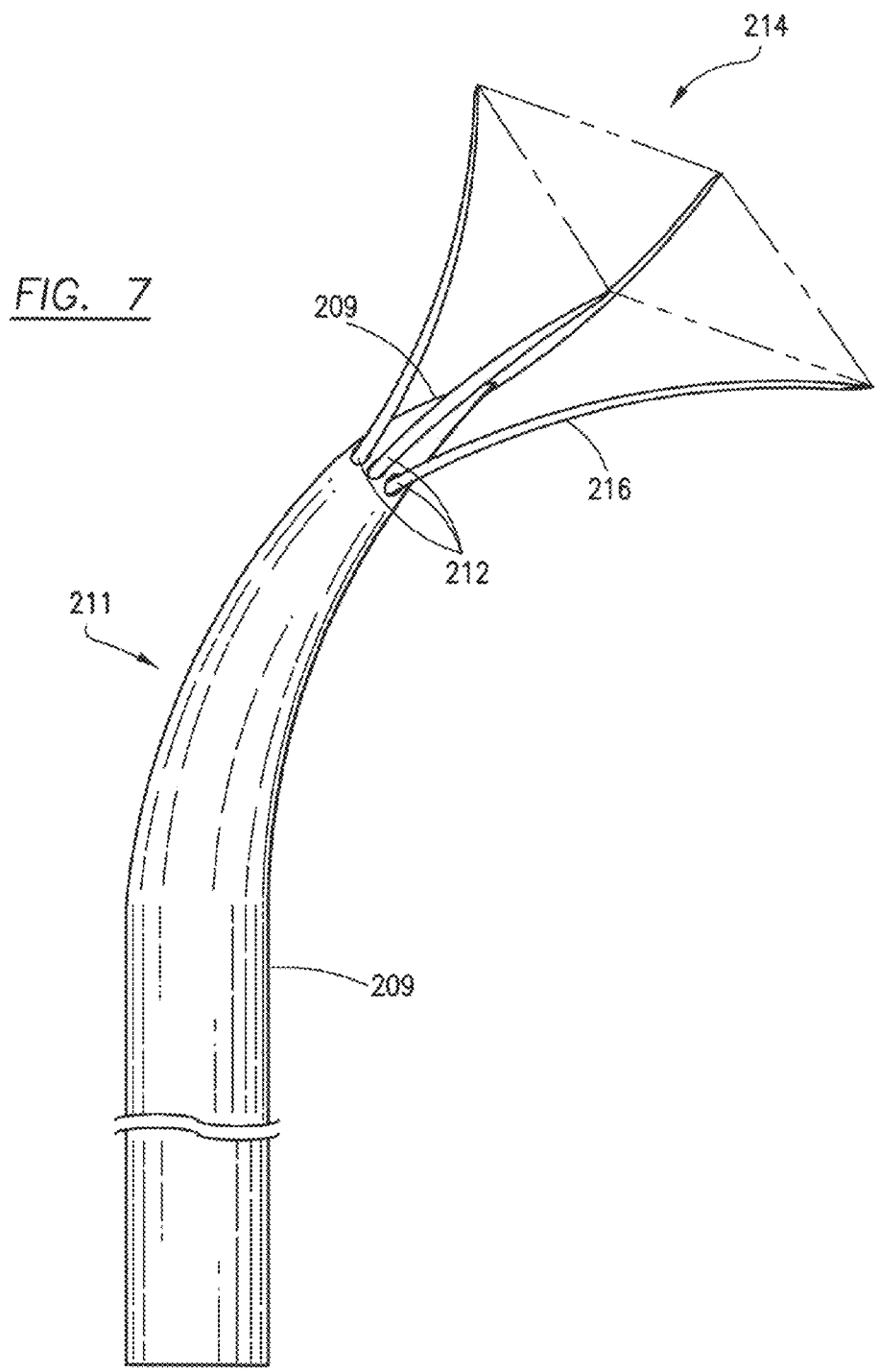
FIG. 7 is a side view of a TIPS needle with four engaging needles in an extended state and the tip of the TIPS needle in phantom built in accordance with the present invention.

Referring back to FIG. 3 shows the device 200 depicted in the extended state. The extended state is the engaging state and is defined by the extension of four (4) engaging needles 216 from the distal end 214 of the TIPS needle 204. The engaging needles 216 are each twenty-three (23) gauge needles made from a semi-rigid material and each has a preformed gentle curve in its tip. The engaging needles 216 pass through the TIPS needle lumen 210, with each engaging needle 216 extending from one of the four needle holes 212 of the TIPS needle 208. Inside the TIPS needle lumen 210, the engaging needles 216 are separated by thin horizontal and vertical septations 218 in the TIPS needle lumen 208. As seen in FIG. 7, while extending, the engaging needles 216 progressively spread apart in a square pattern. When fully extended, the engaging needles 216 lie in a square pattern with 2-3 cm between the needles.

Figure 8:
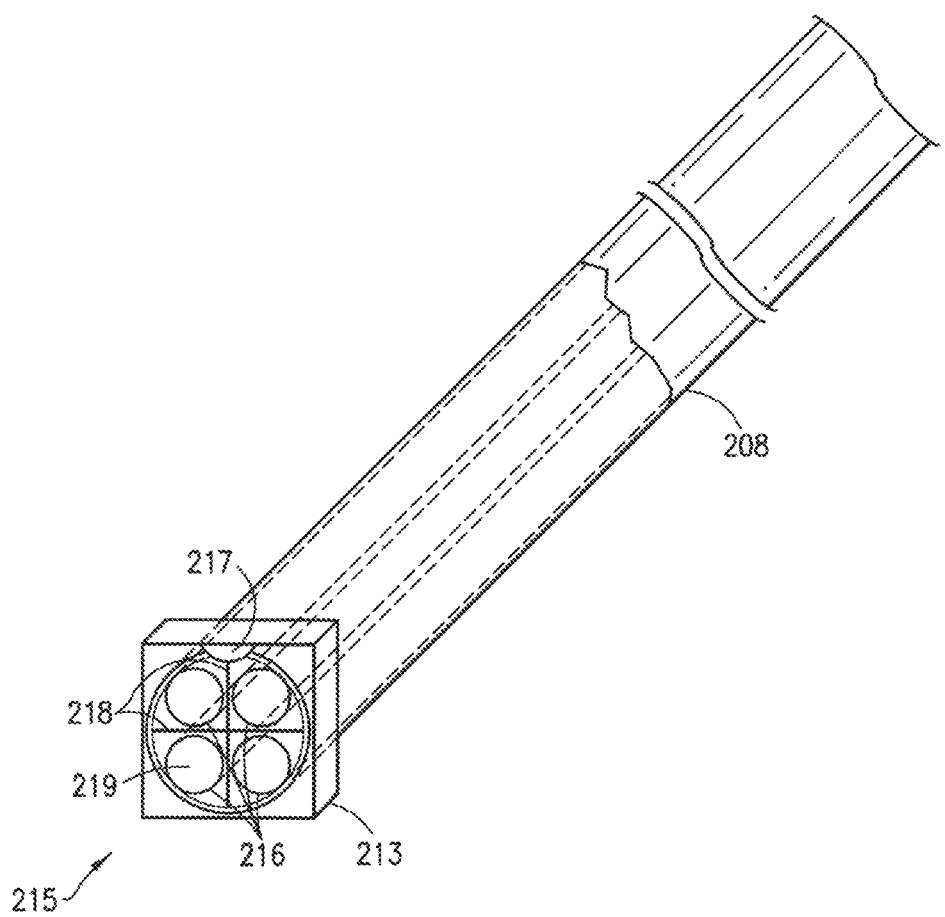
FIG. 8 is a perspective view partially cutaway of the distal end of a TIPS needle built in accordance with the present invention.
Figure 9:
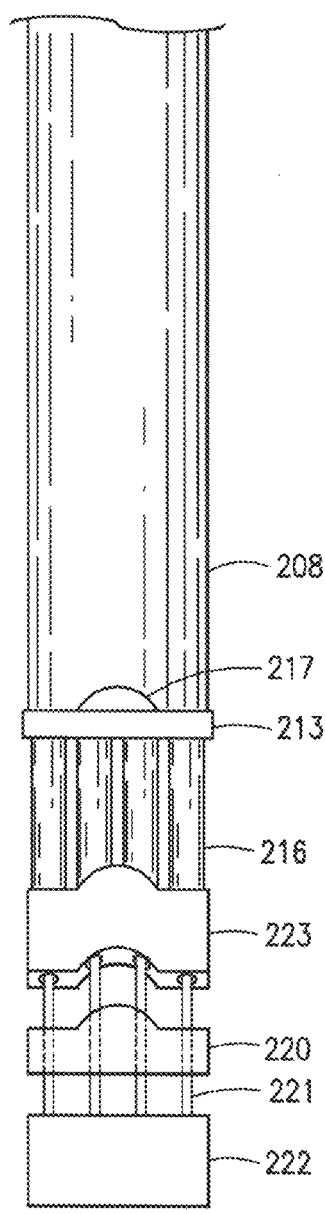
FIG. 9 is a side elevational view of the distal end of a TIPS needle with a needle stylets in partial phantom built in accordance with the present invention.
Figure 10:
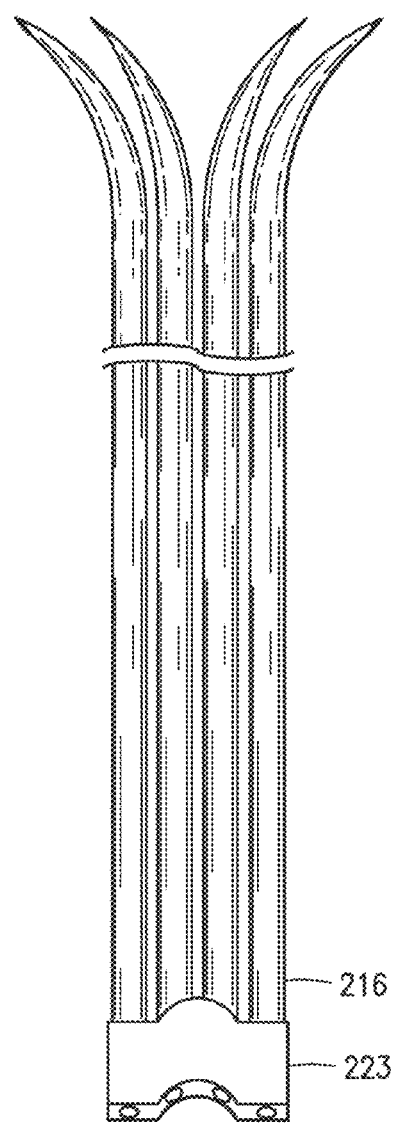
FIG. 10 is a side elevational view of engaging needles and a common needle hub built in accordance with the present invention.
Figure 11:
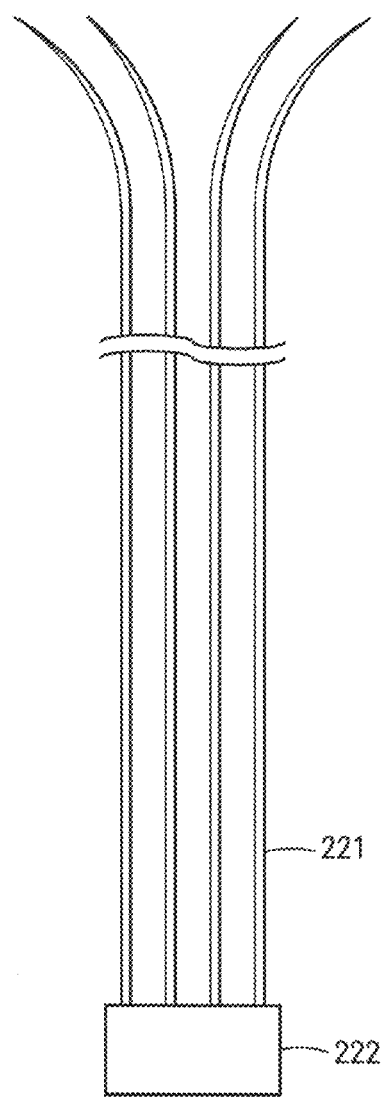
FIG. 11 is a side elevational view of stylets and a common stylet hub built in accordance with the present invention.

Referring now to FIGS. 8, 9, 10, and 11, the primary components that comprise the interior of the device are shown. FIG. 8 shows the proximal end 215 of the TIPS needle 208. At the proximal end 215 of the TIPS needle 208 is the TIPS needle hub 213. The TIPS needle hub 213 serves as the base of the TIPS needle 208 and houses the hub adapter 217. As a result of the horizontal and vertical sepations 218 in the TIPS needle lumen 208, the TIPS needle lumen 208 contains four distinct chambers, each of which can accommodate one engaging needle 216. The engaging needles are each attached to a common needle hub 223, which allows the engaging needles to be advanced and retracted together. To assure that proper pattern of the engaging needles 216 when they are extended from the TIPS needle 208, each engaging needle 216 has a specific target chamber within the TIPS needle 208. If the engaging needles 216 are inserted into the proper chamber, then once the engaging needles 216 are completely advanced into the TIPS needle 208, the common needle hub 223 will engage the hub adapter 217.

Stylets 221, are used to fill the engaging needle lumen 219 and provide additional rigidity to the engaging needles 216 when they are advanced into the engaging needle lumen 219. The stylets 221 are of twenty-three 23 gauge size, made from a semi-rigid material, and are all attached to a common stylet hub 222. In addition, the stylets 221 have the same preformed curve as the engaging needles 216. The stylets 221 are utilized by insertion first through a sliding cover 220, then through the common needle hub 223, and finally through the engaging needle lumen 219.

Figure 12:
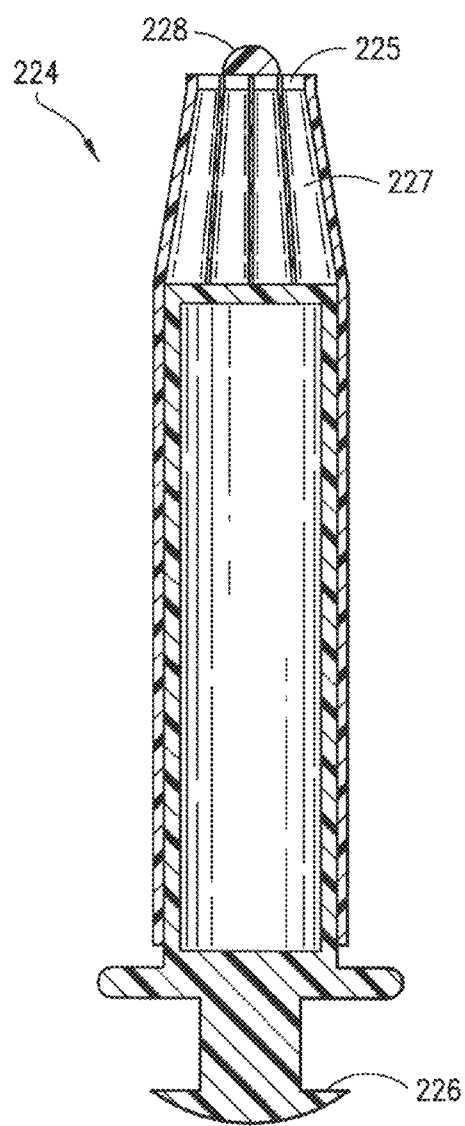
FIG. 12 is a side elevational view in cross section of an aspirating syringe built in accordance with the present invention.

Referring now to FIG. 12, a specially designed syringe 224 is shown. The syringe 224 is a sixty (60) cc syringe that is designed to engage the common needle hub 223 (FIG. 9) and provide aspiration through the engaging needle lumen 219. The syringe has an engaging tip 225 with four independent syringe chambers 227, where each chamber 227 corresponds to one of the four engaging needle lumen 219 (FIG. 8). Along with an opening for each syringe chamber 227, the engaging tip 225 also houses a syringe adapter 228 that fits the common needle hub 223. When syringe 224 is engaged to the common needle hub 223 and the plunger 226 of the syringe 224 is pulled, aspiration is provided through each of the engaging needle lumen 219.

The operation of the device begins with the access of the right hepatic vein 101 (FIG. 1) from the right jugular vein. Under ultrasound guidance, a twenty-one (21) Gauge needle will be used to access the right jugular vein. After obtaining access, a 0.018" wire is advanced through the lumen of the twenty-one (21) Gauge needle and its position confirmed in the superior vena cava with fluoroscopy. A transitional dilator is used to upsize the wire. Catheterization of the right hepatic vein 101 is then performed. Wedge hepatic pressures and portography are performed as needed. The outer sheath 201 and inner dilator are advanced over the wire into the right hepatic vein 101. The inner dilator is then removed and the outer side port 202 is connected to a heparinized saline flush.

Next, the TIPS needle 208 is partially inserted into the inner hub 205 and then the inner sheath 204, so as not to extend the TIPS needle tip 209 beyond the distal end of the inner sheath 204. The assembled apparatus of the TIPS needle 208 and the inner sheath 204 is then inserted into the outer hub 203 and then the outer sheath 201 and extended to the wall of the right hepatic vein 101. Once placed, the inner side port 206 can be connected to a heparinized saline flush as needed.

The engaging needles 216 with their stylets 221 seated are then advanced into the TIPS needle hub 213, but the tips of the engaging needles 216 are not extended through the holes near the end of the TIPS needle 208. At this point, the assembled device will be as shown in FIG. 2. Next, the TIPS needle 208 is slowly advanced a short distance into the hepatic parenchyma anteromedially in the expected direction of the right portal vein 102. The distance that the TIPS needle is advanced into the hepatic parenchyma will likely be around 1 cm, unlike the usual distance of approximately 5 cm that is employed with a typical TIPS apparatus.

Once the TIPS needle 208 is seated in proper position, the engaging needles 216 with their inner stylets 221 are slowly advanced into the hepatic parenchyma. At this point, the assembled device will be as shown in FIG. 3. The engaging needles 216 are advanced approximately 3-6 cm. As the engaging needles 216 are advanced through the needle holes 212 near the end of the TIPS needle 208 into the hepatic parenchyma they will gradually spread apart in a square shape, as depicted in FIG. 7. When fully extended, the tips of the engaging needles will lie in a square pattern with 2-3 cm between the needles. Since the needles progressively spread with further advancement, extending the engaging needles 216 a shorter distance will result in the needle tips lying closer to one another in a smaller square pattern.

The stylets 221 are removed from the engaging needle lumen 219 by pulling on the common stylet hub 222. As the stylets 221 are withdrawn from the engaging needles 216, their tips are covered by the needle cover 220. This needle cover 220 is designed to prevent a needle injury to the operator and to keep the stylet tips together when disengaged from the engaging needles 216. The stylets 221 with their tips covered by the needle cover 220 can then be placed to the side.

With the stylets removed, the syringe 224 is then attached to the common needle hub 223 with each syringe chamber 227 corresponding to one engaging needle lumen 219. The operator then pulls on the plunger 226 to cause an aspirating force through the engaging needle lumen 219 and the tips of the engaging needles 216. The engaging needles 219 are then slowly retracted through the hepatic parenchyma while being aspirated with the syringe 224 by pulling on the syringe 224 together with the common needle hub 223. As the operator retracts the engaging needles 216, the individual syringe chambers 227 are carefully inspected for the presence of portal blood. If blood is not aspirated, the engaging needles 216 can be withdrawn into the TIPS needle 208 and the stylets 221 are replaced into the engaging needle 216. The engaging needles 216 are then advanced in a different direction and the process is repeated until aspiration of blood is successful.

When blood is aspirated into one of these syringe chambers 227, retraction of the engaging needles 216 is immediately stopped. The syringe chamber 227 and corresponding engaging needle lumen 219 containing blood are noted. The syringe 224 is then removed from the common needle hub 223. A small injection of contrast is then made into the engaging needle lumen 219 from which blood was aspirated. This is performed under fluoroscopy to confirm access into the right portal vein 102. Next, under fluoroscopy, a 0.018" wire is advanced into the appropriate engaging needle lumen 219 that had aspirated blood. This wire is advanced well into the right portal vein 102 and then into the main portal vein, splenic vein, or superior mesenteric vein as is necessary to obtain adequate purchase for further intervention.

Once adequate purchase is obtained, the TIPS needle 208 and the attached engaging needles 216 are pulled back as a unit together over the wire. Serial dilatation is then performed over the 0.018" wire and the 0.018" wire is upsized for a larger 0.035" wire. Over the 0.035" wire balloon angioplasty and placement of a covered stent can be performed as is done with a typical TIPS procedure. The procedure is completed with a repeat portogram and measurement of portal pressures as well as potential embolization of varices as required.

With reference to FIGS. 13-19, shown is another embodiment of the present invention providing another suitable and improved means of locating and accessing the portal vein as part of a TIPS procedure.

Figure 13:
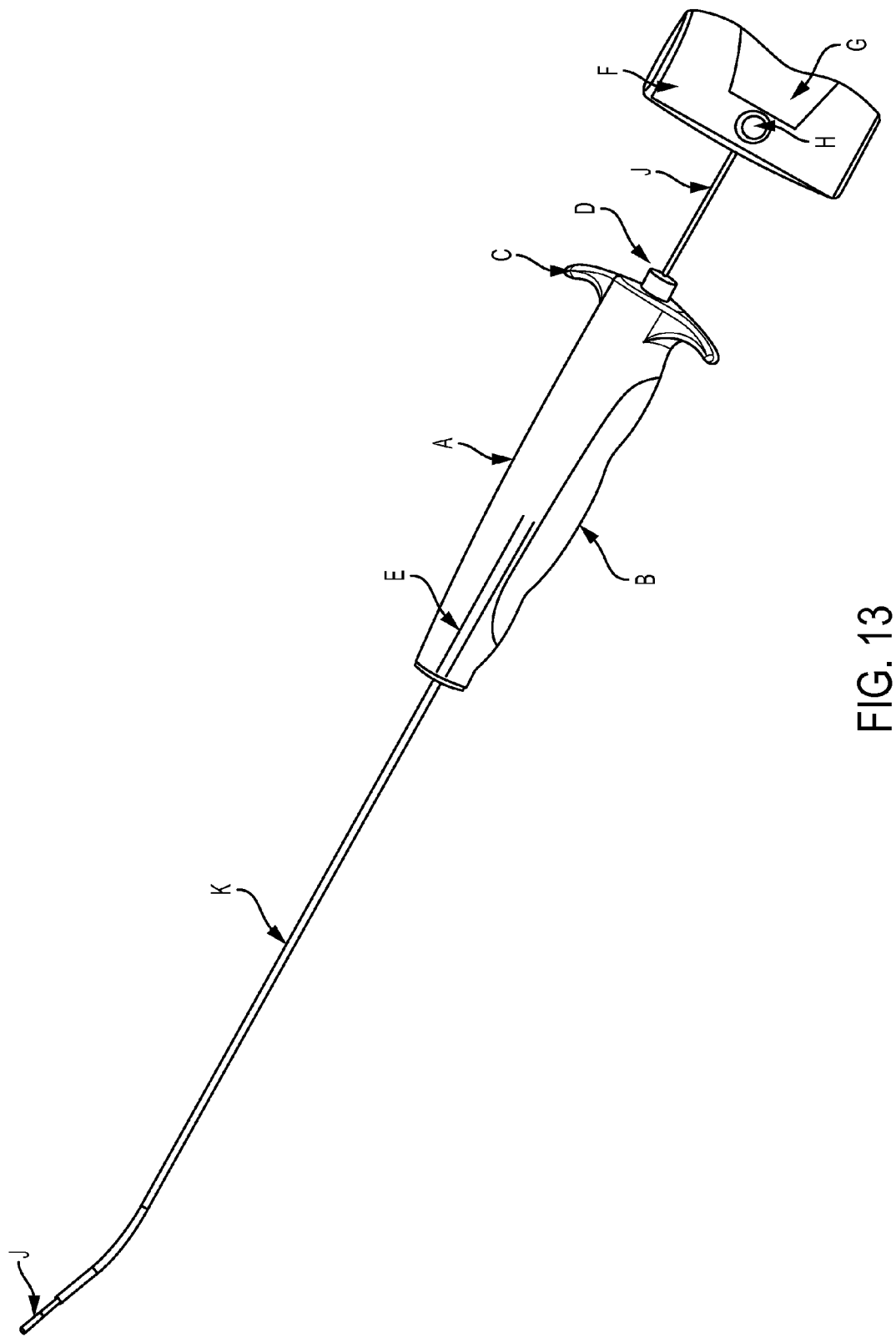
FIG. 13 is a perspective elevational view of another embodiment of the present invention, in a retracted state.
Figure 14:
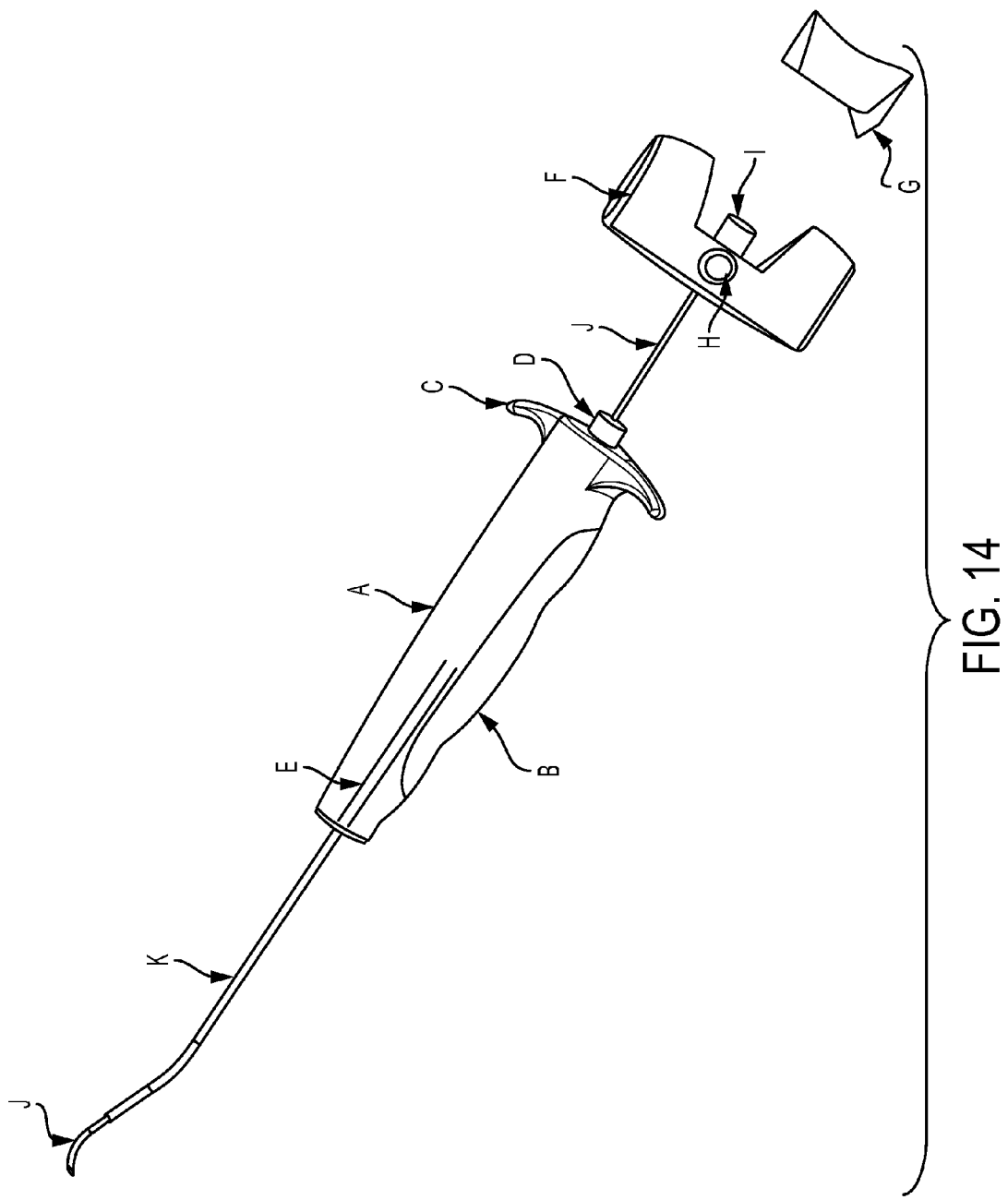
FIG. 14 is a perspective elevational view of another embodiment of the present invention, in an extended state also showing the hub cab removed from the hub.
Figure 15:
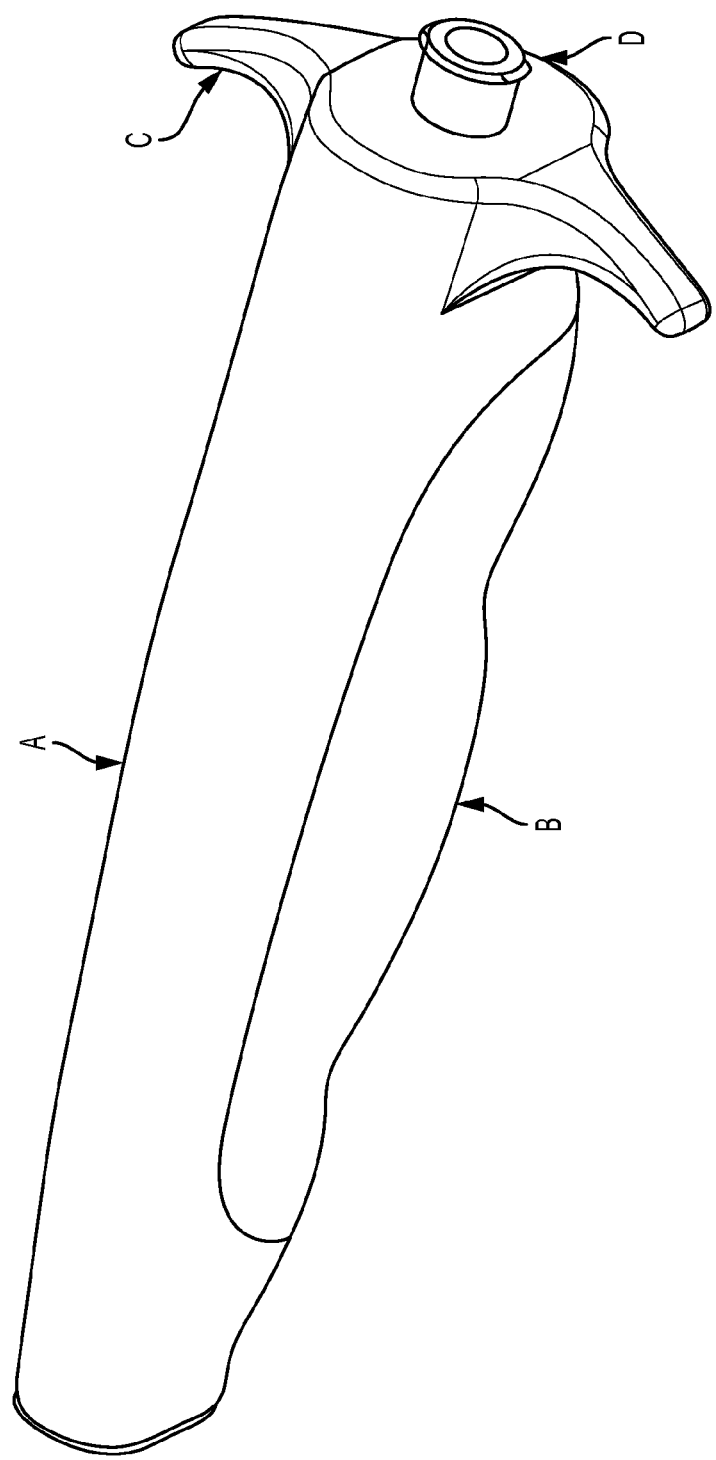
FIG. 15 is a close-up perspective elevational view of another embodiment of the present invention.
Figure 16:
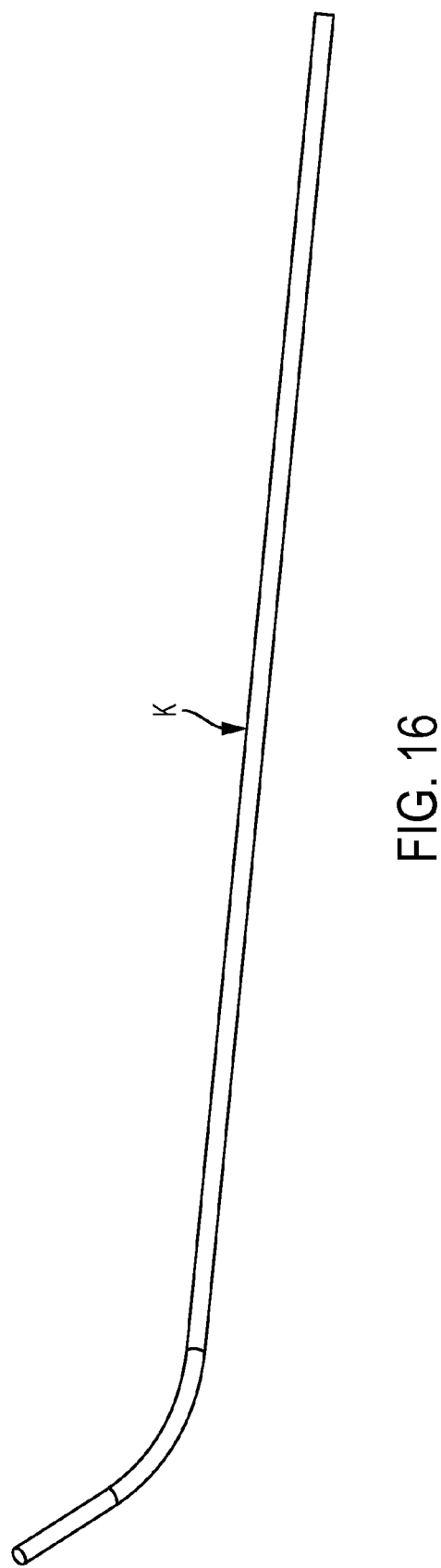
FIG. 16 is a perspective elevational view of the outer guide used in one embodiment of the present invention.
Figure 17:
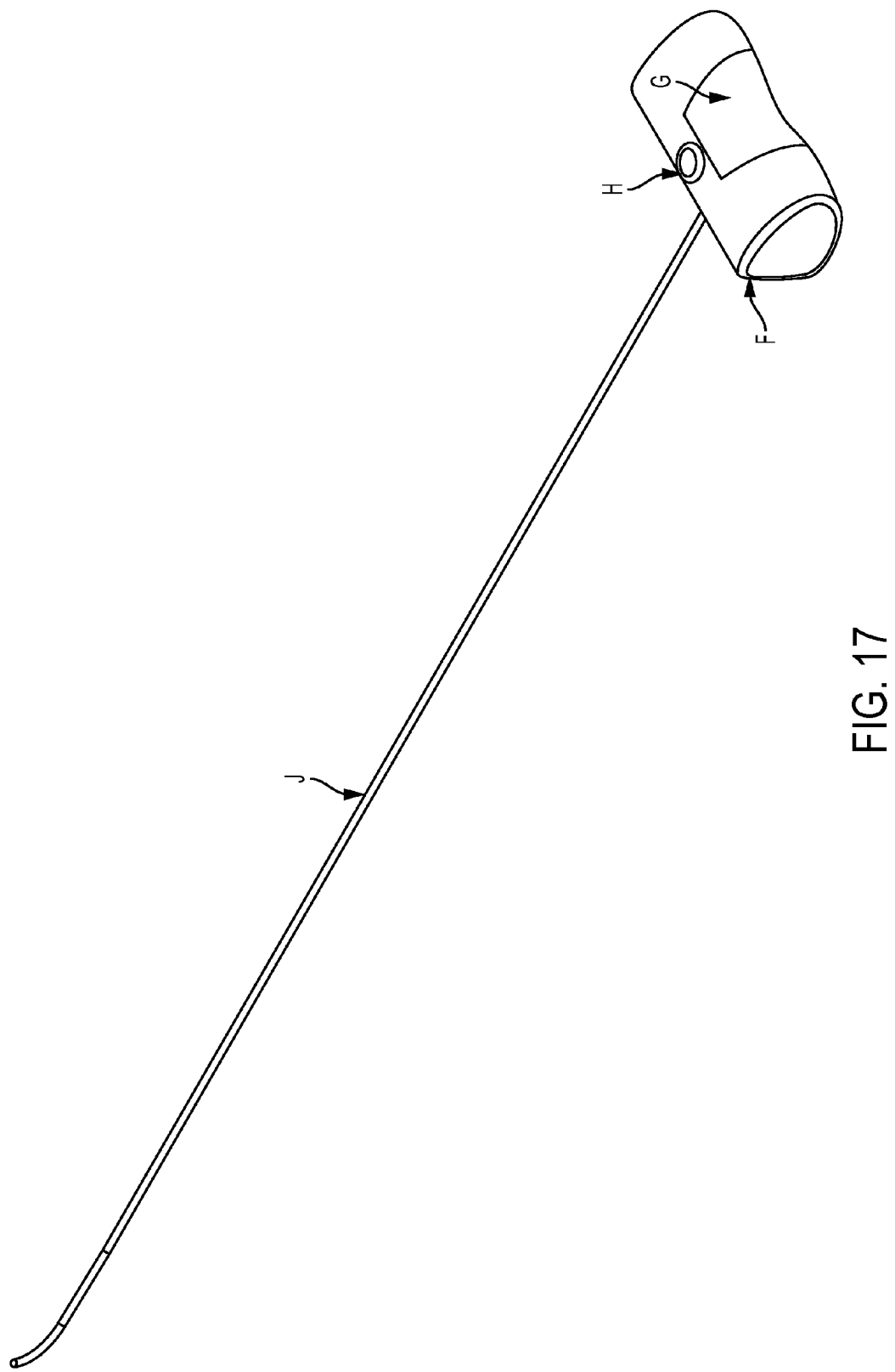
FIG. 17 is a perspective elevational view of the inner needle used in one embodiment of present invention.
Figure 18:
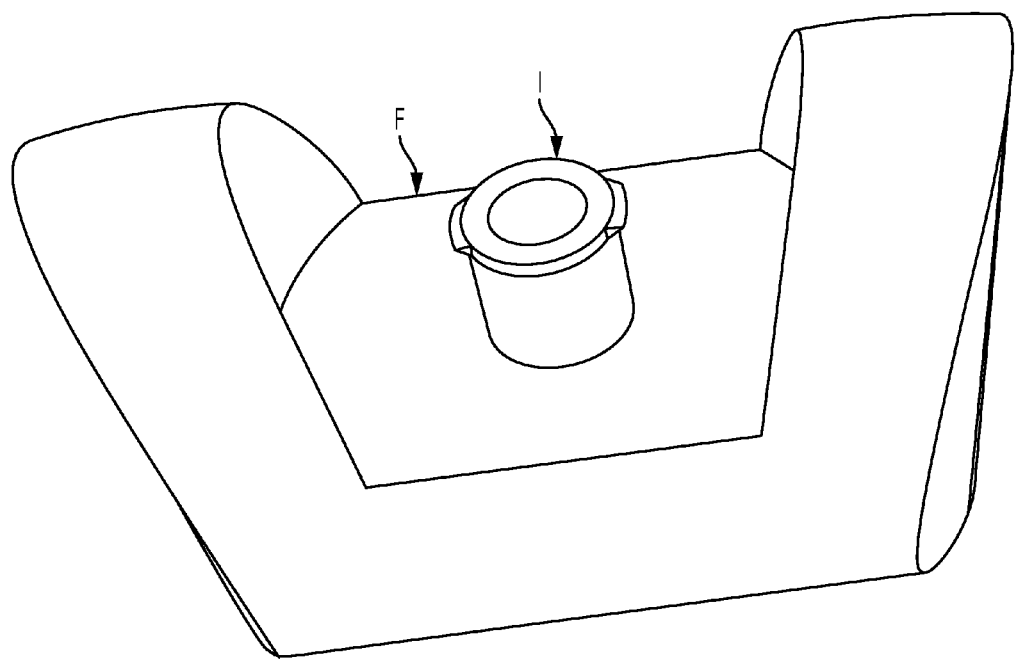
FIG. 18 is a perspective elevational view of the inner needle hub used in one embodiment of the present invention.
Figure 19:
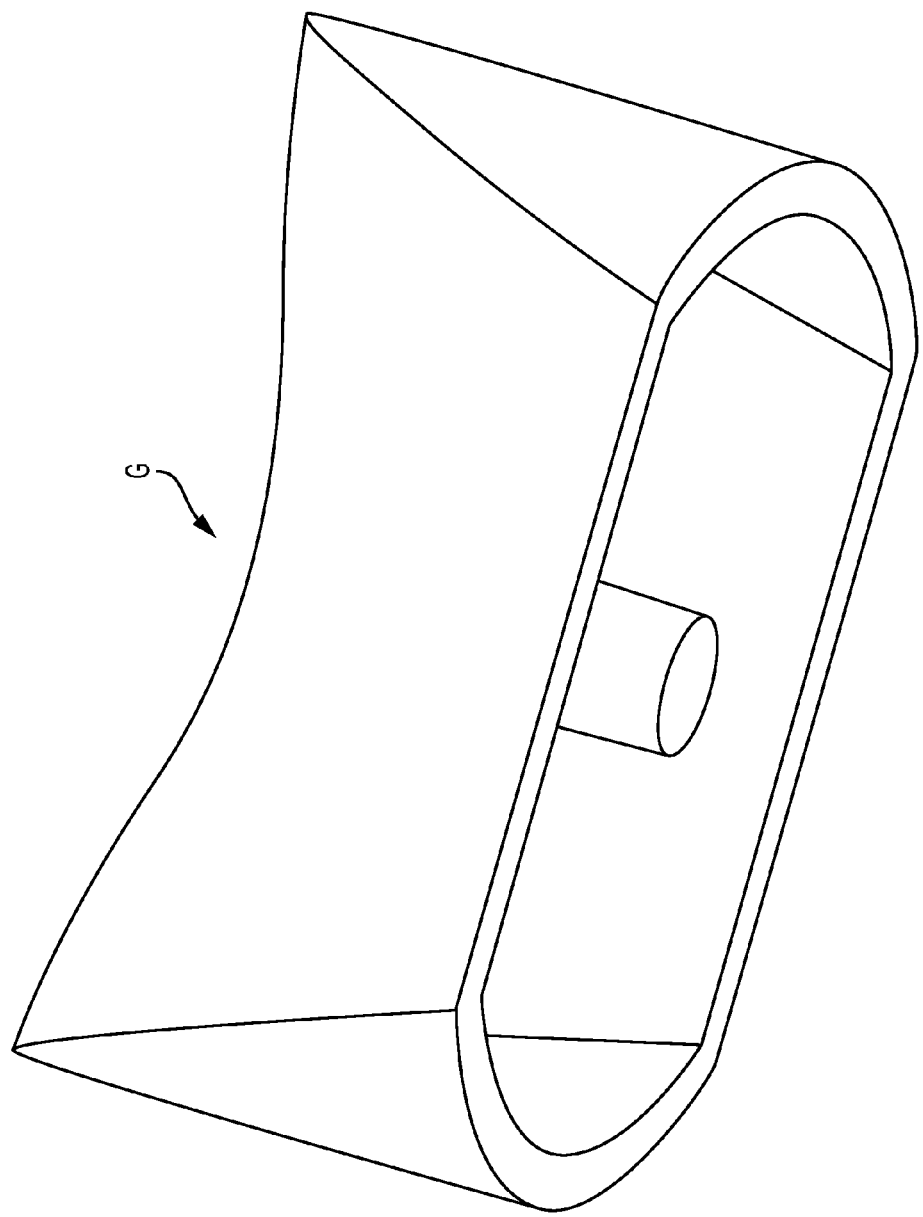
FIG. 19 is a perspective elevational view of the hub cap used in one embodiment of the present invention.

The assembled apparatus shown in FIG. 13 depicts one embodiment of the present invention in an assembled state. An outer handle A (shown alone in FIG. 15) is connected to the outer guide K (shown alone in FIG. 16). The outer handle A has finger grips B along its inferior edge. These grips B allow the operator to torque the outer needle K as desired with one hand (typically the left hand). The outer handle A also has finger winglets C. The winglets are used by the opposite hand (typically the right hand) to assist in the deployment of the inner needle J by providing leverage from which the base of the hand can be pushed against the inner needle hub F. The proximal end of the outer guide K has a luer lock D, which not only allows insertion of the inner needle J into the outer needle K, but also allows attachment of a standard syringe thereto for aspiration or injection as needed. The inner lumen E is disposed within the outer handle A and extends therethrough. In some embodiments, the inner lumen E is just large enough to accommodate passage of a 4 French catheter. The lumen E of the outer handle is in continuity and flow communication with the outer guide K and the luer lock D. In some embodiments, the outer guide K, will measure between 40 and 50 cm and will have a gentle curve at its distal end producing an arc between 20 and 45 degrees. In some embodiments, the end of the outer guide K is flush with no bevel.

The inner needle J is sligingly and removably received in the outer guide, provided through luer lock D, through lumen E and into the outer guide K. At the proximal end of inner needle J is hub F. The hub F has a hub cap G which covers a luer lock I which provides a passage between the hub F and. This luer lock will similarly allow not only passage of a 0.035 inch wire through the hub F and into the inner needle J, but also will allow attachment of a standard syringe for aspiration or injection as needed. The inner needle hub F and the hub cap G are depicted in isolation in FIGS. 18 and 19 respectively, with luer lock I shown in FIG. 18, protruding from the hub F.

The inner needle hub F allows the operator to turn and torque the inner needle J in a 360 degree radius within the outer guide K. This is performed in a 1:1 fashion as the hub F is fixed to the proximal end of the inner needle J. The inner needle hub F has a marker H, which delineates the direction of the curve of the inner needle J so that the operator understands the direction the inner needle J is pointing. This allows the user to manually determine the orientation of the distal tip of the inner needle J without having to rely on imaging such as fluoroscopy.

In some embodiments, the inner needle J will measure between 45 and 55 cm in length and will have a gentle curve at its distal end producing an arc between 20 and 45 degrees. Accordingly, the distal end of the inner needle J will substantially match the curvature and profile of the distal end of the outer guide K. As mentioned, a straight version of the inner needle J with the same length is an alternative embodiment of the present device. Both the straight and curved versions of the inner needle J will have a beveled tip to provide the necessary sharpness to penetrate the parenchyma of the liver. This is dissimilar from the non-beveled distal tip of the outer guide K, which outer guide K need not be used to penetrate the liver.

In some embodiments, the inner needle J has a hydrophilic coating or Teflon coating to reduce the friction between the inner needle J and the outer guide K. As an alternative embodiment of the device, the inner needle may have a 4 French plastic polymer sleeve around the outside of the inner needle J. Such a sleeve will have a luer lock at the end (allowing it to lock to the inner needle hub F), and will closely resemble a standard diagnostic angiographic catheter. The sleeve will advance with the inner needle J during use of the device. The purpose of the sleeve is to reduce friction as well as facilitate catheterization of the portal vein and advancement of the wire once the portal vein is found with the inner needle J.

The operation of this embodiment of the present invention is as follows: As with any standard TIPS procedure, the goal is to create a shunt between the hepatic vein and portal vein using a covered stent as a conduit for blood flow through the liver. This is demonstrated in FIG. 1 where blood flows from the portal vein, 102, to the hepatic vein, 101. Typically this involves communication between the right hepatic vein and the right portal vein, but variations on this exist depending upon the patient's anatomy and the need for additional shunting.

Using standard angiographic technique, catheterization of the right jugular vein, the inferior vena cava, and then hepatic vein (typically right) is obtained. After confirming appropriate hepatic vein catheterization, a stiff wire is placed distally within the vein. Over the stiff wire, a 10 French sheath is advanced well into the hepatic vein. At this point, wedged portal pressures and wedged portography with an occlusion balloon can be performed at the operator's discretion to delineate the location of the target portal vein and assess the degree of portal hypertension.

The apparatus of the present invention is then inserted through the sheath and is advanced to the tip of the sheath. The assembled apparatus is advanced such that the inner needle J and hub F are retracted so that the sharp tip of the inner needle J initially does not extend beyond the tip of the outer guide K. Once the distal tip of the assembled apparatus reaches the tip of the sheath, the sheath is gently withdrawn to expose the outer guide K.

Using the outer handle A the apparatus is rotated in the general expected direction of the target portal vein. The operator then stabilizes the outer handle A and therefore outer guide K, with his or her left hand. The inner needle hub F is then rotated with the operator's right hand in the expected direction of the target portal vein to fine tune the targeting of the portal vein. Using the right hand, two fingers are placed on the finger winglets C. The base of the right hand is then used to apply pressure to the base of the inner needle hub F, advancing the distal tip of the inner needle J into the liver parenchyma.

The hub cap G of the inner needle hub F is then removed, exposing the luer lock I of the needle hub F. A saline containing syringe is attached to luer lock I and a small amount is injected to clear the lumen of the inner needle J. The saline syringe is removed, and a contrast dye syringe is attached. A combination of gentle aspiration and short puffs of contrast dye are made while the inner needle J and inner needle hub F are slowly retracted back towards the outer guide K. Once the portal vein is found, a wire can be directly advanced through the lumen of the inner needle J into the portal vein or alternatively, the sleeve of the inner needle J can be advanced over the inner needle, J into the portal vein at which time the inner needle J and inner needle hub F can be removed. If the portal vein is not found on initial deployment of the inner needle J the hub cap G can be replaced, and then the inner needle J and inner needle hub F can be rotated to a new orientation and the process repeated until the portal vein is found.

Regardless of the exact technique, once a wire is successfully advanced into the portal vasculature, the remainder of the TIPS procedure is completed with standard technique. This requires advancement of a 4 French catheter over a wire and through the outer guide handle A, and outer guide K, into the portal vein. The initial wire advanced is then exchanged for a stiffer wire over which a diagnostic 4 French flush catheter can be advanced and used to perform portography and obtain portal pressures. The stiff wire is replaced and the diagnostic flush catheter removed. Now, the outer guide K and outer handle A can be safely removed. The tract through the liver parenchyma is then balloon dilated until the 10 French sheath can be successfully advanced from the hepatic vein through the liver parenchyma into the portal vein. Once the sheath is advanced into the portal vein, the TIPS stent is deployed per the manufacturer's IFU and the diameter adjusted with balloon angioplasty until the desired portosystemic gradient is obtained.

The instant invention has been shown and described herein in what is considered to be the most practical and preferred embodiment. It is recognized, however, that departures may be made there from within the scope of the invention and that obvious modifications will occur to a person skilled in the art.

What is claimed is:

1. A device used for establishing a transjugular intrahepatic portosystemic shunt quickly by locating a portal vein in a liver for receiving the shunt comprising:
    an elongated hollow outer guide;
    an outer handle having an inner lumen and a first luer lock, the outer handle attached at a proximal end of the outer guide, the outer guide in flow communication with the inner lumen and the luer lock;
    an elongated hollow inner needle;
    a hub having a second luer lock, the hub attached at a proximal end of the inner needle, the inner needle in flow communication with the second luer lock;
    wherein the inner needle is slidingly received through the first luer lock and into the outer guide through the inner lumen;
    wherein the inner needle is configured to rotate within the outer guide by manipulation of the hub; and
    wherein a distal tip of the inner needle is deployed out of and beyond a distal tip of the outer guide, the distal tip of the inner needle configured to be advanced into the parenchyma of the liver to locate the portal vein.

2. The device of claim 1, wherein the inner needle is capable of aspirating fluid therethrough.

3. The device of claim 1, further comprising a hub cap removably received on the hub.

4. The device of claim 1, further comprising finger winglets on the outer handle to assist in deployment of the inner needle.

5. The device of claim 1, further comprising a marker on the hub providing an indication of the orientation of the inner needle.

6. The device of claim 1, wherein the distal tips of the outer guide and the inner needle have matching curved geometry.

7. A method for quickly locating a liver portal vein necessary for performing a transjugular intrahepatic portosystemic shunt procedure comprising:
    providing a device comprising an elongated hollow outer guide having an outer handle at its proximal end, the outer guide slidingly receiving an inner needle, the inner needle having a hub at its proximal end, the inner needle configured to rotate within the outer guide;
    catheterizing, through the jugular vein, a liver hepatic vein of a patient receiving the transjugular intrahepatic portosystemic shunt;
    inserting the device into the jugular vein and through to the liver hepatic vein;
    rotating the outer handle of the device until the outer guide is in the expected direction of the liver portal vein;
    stabilizing the outer handle and rotating the inner needle by way of the hub in the expected direction of the liver portal vein;
    applying pressure to the hub and advancing the distal tip of the inner needle into the parenchyma of the liver, through the wall of the of the hepatic vein in a direction towards the portal vein;
    creating an aspirating force inside the inner needle to locate the liver portal vein; and
    establishing a shunt to the portal vein.

* * * * *